United States Patent [19]

Rabussier et al.

[11] 3,961,040

[45] June 1, 1976

[54] INSECTICIDAL EVAPORATOR HAVING A DIFFUSION LAYER OF OLEFIN POLYMERIZATE

[75] Inventors: Bernard Rabussier, Aventon; Jean-Pierre Mandon, Poitiers, both of France

[73] Assignee: Airwick Industries, Inc., Carlstadt, N.J.

[22] Filed: Mar. 13, 1974

[21] Appl. No.: 450,935

[30] Foreign Application Priority Data

Mar. 16, 1973 Luxemburg............................ 67231

[52] U.S. Cl..................................... 424/33; 424/19; 424/78; 424/83; 424/219; 239/53
[51] Int. Cl.² ..................... A01N 17/00; A01N 9/36
[58] Field of Search ................ 239/53, 56; 424/219, 424/33, 83

[56] References Cited
UNITED STATES PATENTS 3,781,428 12/1973 Hennart et al...................... 424/219

*Primary Examiner*—V. D. Turner
*Attorney, Agent, or Firm*—Frederick H. Rabin; Harry Falber; Heinrich W. Herzfeld

[57] ABSTRACT

An insecticidal evaporator is described which comprises

I a liquid composition containing
  a. 40 to 90% by weight approximately calculated on the total weight of the composition of a volatile insecticidal ester of phosphoric acid the vapor pressure of which is at least $10^{-3}$ Torr at 20°C;
  b. at least one first additional organic liquid compound having a vapor pressure less than or equal to that of the volatile insecticidal ester;
  c. at least a second additional organic compound miscible or soluble in the mixture of the volatile insecticidal ester and of the first additional compound;
II. a fibrous mass absorbent for the said composition I, and impregnated by the same; and
III a diffusion layer covering at least a part of the surface of the said fibrous mass, the remainder of the surface of the fibrous mass being covered by an envelope impermeable to the said composition.

8 Claims, No Drawings

INSECTICIDAL EVAPORATOR HAVING A DIFFUSION LAYER OF OLEFIN POLYMERIZATE

The present invention concerns improvements in insecticidal evaporating devices having an olefin polymer duffusion wall. French Pat. Specification No. 1590647 describes a device having a non-porous permeable wall or diffusion layer for the emission of vapours of insecticidal phosphoric esters, particularly vapours of DDVP.

Such an apparatus has a number of advantages, in particular a regular functioning and long service life and good stability in storage lasting for long periods.

Systems using porous walls are also known but these do not have the advantage of giving a sufficiently constant diffusion; they also suffer from the disadvantage that they do not constitute a sufficient barrier to the take up of atmospheric water by the active material and by the evaporative support.

Experience of the applicants has shown that devices with non-porous walls which have been stocked, and packaged for long periods of time can appear when they are put into service different from those devices freshly manufactured.

In effect on opening it happens that the exterior face of the permeable walls appears to be dampened by DDVP and in certain cases several droplets of liquid can even emerge above the grill.

The explanation of such a phenomenon which is called exudation has not yet been found and the applicant has been able to verify that it does not occur systematically during the assembly of the samples manufactured.

The cases where it has been observed correspond in general to those where storage periods in packing are greater than 1 year for conditions of storage at ambient temperature.

It has been established on the other hand that the higher the temperature of storage, the more quickly is the phenomenon likely to appear (about 1 month at 40°C); inversely at low temperature (0°C) the phenomenon does not occur.

In any case the exudation makes no difference whatever to the good stability of the device during storage and the liquid droplets observed on opening disappear a few hours after the device has been put to use.

Nonetheless for a user ignorant of these facts, the appearance of the device on opening is disagreeable and prejudices a good impression being given by the product. Furthermore once exudation has reached a stage where there have emerged several larger drops of liquid, there is a risk of causing stains and a risk of contacting the toxic active material with the user's fingers when the device is put to use.

Compositions containing phosphoric esters of the DDVP type impregnated on fibrous supports necessitate the presence of a stabiliser to avoid decomposition of the DDVP during storage and during the service life.

Among stabilising agents known for stabilising phosphoric esters there have been recommended for a long time epoxidised liquid compounds such as, particularly epoxised unsaturated vegetable oils e.g. epoxidised soya oil, preferably with minimum of 6% oxirane oxygen, glycidyl ethers of aliphatic monoalcohols having preferably 8 to 18 carbon atoms such as for example n-dodecanol glycidyl ether, glycidyl ethers of diols such as for example the diglycidyl ether of 2,2-butanediol and the diglycidyl ether of Bis-phenol A, epoxidised esters of mono- or di-carboxylic aliphatic acids preferably having 6 to 24 carbon atoms, in particular epoxidised $C_1$ to $C_6$ alkyl adipates and sebacates and epoxidised $C_5$ to $C_{12}$ cycloalkyl adipates and sebacates, for example epoxidised cyclohexyl adipate.

The use of liquid epoxidised compounds in the evaporators of the type described in French Pat. Specification No. 1590647 has been recognised by the applicants as giving rise in certain storage conditions to a substantial exudation before the device is put to use.

The object of the present invention is to provide an insecticidal evaporative device of the type noted above in which the phenomenon of exudation is considerably reduced or even practically eliminated.

This object is obtained without compromising the stability of the active material by providing an insecticidal evaporator comprising:

I a liquid composition containing;
  a. 40 to 90% by weight calculated on the total weight of the composition of a volatile insecticidal phosphoric acid ester the vapour pressure of which is at least $10^{-3}$ Torr at 20°C;
  b. at least a first additional organic liquid compound having a vapour pressure less or equal to that of the insecticidal volatile ester;
  c. at least a second additional organic compound miscible with or soluble in the mixture of the volatile insecticidal ester and the first additional compound;

II an absorbant fibrous mass impregnated by the said composition (I); and

III a diffusion layer covering at least a part of the surface of the said fibrous mass, the remainder of the surface of the said fibrous mass being covered by an envelope impermeable to the said composition;

the said first additional compound favouring, or at least not significantly reducing, the exudating of the insecticidal volatile ester contained in the said diffusion layer; in which evaporator:

i. the said diffusion layer is non-porous, and consists essentially of an olefin polymer having a thickness of less than 150 microns, and
  ii. the said organic compound (c) is an agent reducing the exudation of the volatile insecticidal ester and has a vapour pressure of less than 0.2 Torr at 25°C, and the sum of the properties of the said agent as defined by the expression:

$$\log P + 7.5 \frac{\mu \cdot d_4^{25}}{\epsilon} \tag{A}$$

is equal to from 2.4 to 3.4, in which expression:
  P represents the vapour pressure at 25°C expressed in $10^3$ torr,
  $\mu$ represents the dipolar moment at 25°C expressed in $10^{18}$ (C.G.S.) electrostatic units,
  $d_4^{25}$ represents the density at 25°C relative to that of water at 4°C and
  $\epsilon$ represents the dielectric constant of the said compound, at 20°C, the amount of the said compound (c) in the evaporator ranging from 1 to 40% by weight calculated on the total weight of the composition (I).

The present invention likewise comprises a method for reducing the exudation of the insecticidal ester in an evaporator described above by the application of the measures defined under (i) and (ii) above.

In practice the quantity of liquid composition (I) impregnated in the fibrous mass (II) is completely absorbed thereby.

Preferably the first additional compound is an epoxidised liquid compound having a vapour pressure less than or equal to that of the insecticidal volatile ester.

The agent reducing the exudation defined under (ii) is preferably an aromatic compound and in particular an aromatic derivative of benzene or naphthalene.

The number of aliphatic organic compounds miscible or soluble in a mixture of the volatile insecticidal ester and of the said first additional compound (b) which fulfil the conditions defined under (ii) by the expression cited above and which are at the same time industrial products easily obtained on the market is quite limited.

Most readily available are the aromatic organic compounds and among those especially compounds falling under the formula

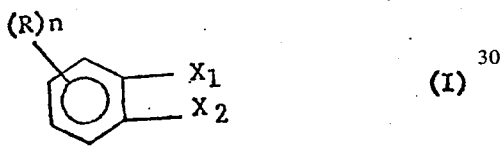

in which
X$_1$ represents a hydrogen atom, and
X$_2$ represents a hydrogen atom or one of the substituents mentioned below in the definition of (R)$_n$,
or
X$_1$ and X$_2$ together represent a divalent bridge of the formula —CH=CH—CH=CH—; and
(R)$_n$ represents a substituent on the benzene nucleus in the formula which is chosen from among
a. 2 to 3 hydroxyl groups (—OH);
b. 1 to 3 alkyl groups each having 1 to 4 carbon atoms;
c. 1 to 2 alkyl groups having 1 to 4 carbon atoms together with a hydroxyl group, one of which substituents (a) to (c) may occupy the X$_2$ position, as stated supra, or
d. an alkoxy group having 1 to 4 carbon atoms.

It is to be noted that phenol itself does not afford a satisfactory reduction of the exudation.

The applicant has thus found that, surprisingly and for hitherto unexplained reasons, it is possible considerably to reduce the exudation in DDVP evaporators comprising a diffusion layer which is non-porous and of polyolefinic material, by incorporating in the impregnating solution used in the said device a quantity of from 1 to 40%, relative to the total weight of the composition, of at least one compound as defined above under (ii).

The invention envisages evaporative insecticidal devices comprising preferably as essential insecticidal constituent:
40 to 90% of an insecticidal compound chosen from volatile phosphoric esters defined by the formula:

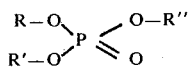

in which R and R' are the same or different and represent alkyl groups containing 1 to 4 carbon atoms, R'' being chosen from one of the two following groups:

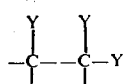

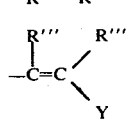

in which Y is chosen from among halogen of atomic weight no greater than 80, R''' and R'''' are the same or different and are chosen from hydrogen, the said halogen atoms, methyl and ethyl.

As non-limited examples of esters corresponding to formula II above the following phospheric esters may be noted:
2,2-dichloro-vinyl dimethyl phosphate,
2-chloro-vinyl dimethyl phosphate,
2,2-dichloro-vinyl diethyl phosphate,
2-chloro-vinyl diethyl phosphate,
2-chloro-vinyl diisopropyl phosphate,
2-chloro-vinyl dibutyl phosphate,
2-chloro-vinyl diisobutyl phosphate,
2,2-dibromo-vinyl dimethyl phosphate,
2-bromo-vinyl dimethyl phosphate,
2-bromo-vinyl diethyl phosphate,
2-bromo-2-chloro-vinyl dimethyl phosphate,
2-bromo-vinyl diethyl phosphate,
2,2-dichloro-vinyl ethyl methyl phosphate,
1,2-dibromo-2,2-dichloro-ethyl dimethyl phosphate,
1-bromo-2,2,2-trichloro-ethyl dimethyl phosphate,
1,2,2,2-tetrabrom-ethyl dimethyl phosphate,
1,2-dibromo-2,2,-dichloro-propyl dimethyl phosphate
2-chloro-1methyl-vinyl dimethyl phosphate,
2-chloro-2-methyl-vinyl dimethyl phosphate,
2,2-dichloro-1-methyl-vinyl dimethyl phosphate,
2-chloro-1-ethyl-vinyl dimethyl phosphate,
2-chloro-2-ethyl-vinyl dimethyl phosphate,
2-chloro-1,2-dimethyl-vinyl dimethyl phosphate,
2-chloro-1methyl-vinyl diethyl phosphate.

From the point of view of the present invention the preferred esters among those which have just been noted are those in which the group R'' is a group —CH=CCl$_2$, i.e. 2,2-dichloro-vinyl dialkyl phosphates; preferred among these is 2,2-dichloro-vinyl dimethyl phosphate, known under the common designations DDVP and DICHLORVOS.

The content of the phosphoric ester in the active composition is preferably between 60 and 80% calculated on the weight of composition (I).

As the active liquid composition should preferably be homogenous, it follows that the organic compound reducing exudation should preferably be miscible with the phosphoric ester or soluble in this ester and also it goes without saying that the compound reducing exudation should not be liable to react chemically with the phosphoric ester.

To obtain a particularly substantial reduction in the exudation, the value of the expression;

$$\log P + 7.5 \frac{\mu \cdot d_4^{25}}{\epsilon} \qquad (A)$$

is preferably between 2.6 and 3.2.

The active composition can also contain other ingredients and particularly other stabilisers for the insecticidal phosphoric ester.

In the production of insecticidal evaporators according to the invention the active composition is absorbed on a fibrous mass which represents from 30 to 60% by weight of the total weight of the active composition and of the support combined.

Preferably the fibrous mass represents 40 to 50% of the total weight of the active composition and the support combined. Advantageously the fibrous mass is present in the form of a sheet or a laminate of several sheets.

The absorbant fibrous mass is preferably formed by cellulosic material such as for example: strong unsized paper, unsized cellulose cardboard, felted cardboard or a cardboard made from old papers.

The non-porous diffusion layer which should preferably be in intimate contact with the fiber ends on the surface of the fibrous mass preferably has a thickness between 15 and 80 microns and is advantageously obtained by extrusion-lamination on to the fibrous material before the impregnation of the latter with the active composition.

Among the olefin polymers forming the non-porous diffusion layer there may be noted as non-limitative examples; polyethylenes of any density, polypropylene, copolymers of ethylene with other olefinic compounds and terpolymers of ethylene with acrylic acid. The preferred group of olefinic polymers for making insecticidal evaporators according to the invention is that of terpolymers of ethylene with acrylic acid and at least one acrylic ester, the content of polymerised ethylene in the terpolymer being preferably between 70 and 95% by weight.

The remainder of the polymer is preferably composed of at least approximately equal portions of the acid and the arylic ester. Preferably the acrylic ester is methyl or ethyl acrylate or methacrylate.

With the compounds defined under (ii) there is obtained a reduction of at least 65% and in some cases of 95% of the phenomenon of exudation which appears in the known evaporators described above, with or without the addition of a hydrophobic diluent miscible with DDVP chosen from among the compounds defined under I (b), such as for example a dialkyl phthalate in which the alkyl groups have 1 to 12 and preferably 4 to 8 carbon atoms, for example:

1-dibutyl phthalate,
dihexyl phthalate, or
dioctyl phthalate.

Among the compounds defined under (ii) particulary satisfactory results have been obtained with:

TABLE I

| Name of compound | Value of the expression (A) noted above | Vapour pressure in torr at 25°C |
|---|---|---|
| 1. hydroquinone | 2.5 | 0.0004 |
| 2. resorcinol | 3.2 | 0.0025 |
| 3. carvacrol | 2.7 | 0.05 |
| 4. thymol | 2.6 | 0.05 |
| 5. 2,4-dimethyl-phenol | 3.35 | 0.16 |
| 6. 3,4-dimethyl-phenol | 2.7 | 0.039 |
| 7. 3-nitro-anisol | 2.6 | 0.02 |
| 8. 2-ethoxy-naphthalene | 3.0 | 0.007 |
| 9. 6-t-butyl-2,4-dimethyl-phenol | 2.7 | 0.012 |
| 10. 1-methyl-naphthalene | 3.25 | 0.067 |
| 11. 2-methoxy-naphthalene | 3.15 | 0.011 |
| 12. di-(2-chloroethoxy)-methane | 3.2 | 0.08 |
| 13. 2-propyl-phenol | 3.0 | 0.033 |
| 14. 2,3-dimethyl-napthalene | 3.1 | 0.011 |

The content of the compound defined under (ii) is preferably between 3 and 10 % calculated on the total weight of the composition (I).

COMPARATIVE EXAMPLE

A series of 48 evaporators of known type was made each having on opposite sides thereof a diffusion layer constituted by a coating of low density polyethylene (0.915 g/cm³) 18 microns thick, intimately adherent to a supporting plate or sheet of unsized cardboard weighing 360 g/m². Between the two cardboard sheets which support the diffusion layers two sheets of felted cardboard are interposed which are able to absorb at least 30 g of active solution.

An assembly of four such cardboard sheets, the total weight of which is 21 g, is lodged in a square polyethylene frame with a protective grill, the diffusion layers bearing permeation surfaces being welded along their edges to the frame of the device. After mounting and welding on the frame the total permeation surface of the device is 200 cm². The impregnation of the two felted cardboard sheets takes place with the aid of a syringe through a recloseable orifice situated in the rim of the frame. The protection of the device during storage is obtained with the aid of two sealing foils each consisting of a layer of polyethylene and a layer of terephthalic polyester extruded together and laminated with a foil of alumunium which foils are welded to the frame to cover the permeation surfaces prior to use.

In this example each evaporator is charged with 30 g of a solution having the following composition (in percent by weight):

| | |
|---|---|
| DDVP | 70 % |
| diethylhexylphthalate | 15 % |
| epoxidised soybean oil | 14.5 % |
| stabilising diazene | 0.5 % |

The evaporators are stored in an oven at 40°C in groups of 12 units and at the end of the time noted below the sealing foils were removed in order to determine whether any exudation had taken place. For this purpose, the permeation surfaces, the frame, the grills and the internal faces of the sealing foils were washed with acetone. Thereafter the quantity of DDVP present in the washing solution was determined.

| Storage time at 40°C | Maximum exudation of 12 evaporators |
|---|---|
| 1 month | 325 mg of DDVP |
| 2 month | 350 mg of DDVP |
| 3 month | 480 mg of DDVP |
| 4 month | 465 mg of DDVP |

As stabilising diazene one can use one of the compounds of this class described in British Pat. Specification No. 1,308,951; preferably there is used an azoic dyestuff such as the following diazenes:

Diazene A: 1-(4-phenylazophenylazo)-2-ethylaminonaphthalene
Diazene B: 1-(4-methyl-2-nitro phenylazo)-3-ethoxycarbonyl-4,4-dimethyl-2,6-dioxo cyclohexane
Diazene C: 1-phenylazo 2-naphthol
Diazene D: 4-phenylazo-N,N-diethylaniline or a complex formed with metals such as for example chromium, nickel, copper or cobalt, and preferably one of the mixtures of complexes as follows:

Diazene D: the mixture of the (1:2) complexes of chromium of the following azo dyestuffs:

1-(2-hydroxy 5-nitro phenylazo)-2-naphthol, sodium salt (3.4 mol)
1-(2-hydroxy 4-nitro phenylazo)-2-naphthol, sodium salt (8.3 mol)
1-(2-hydroxy 3-nitro 5-tert.amyl phenylazo)-2-naphthol, sodium salt (0.3 mol)

Diazene E: the mixture of the chromium complexes (1:2) of (2-amino 5-nitro-1-ethylsulphonyl phenol) 2-(2-carboxy phenyl)-naphthylamine, sodium salt and (2-amino 5-nitro-4-ethylsulphonyl phenol) 8-hydroxyquinolene, sodium salt.

EXAMPLES 1 TO 13

13 series of evaporators were prepared only differing from those of the comparative example by the composition of the impregnation solution. Table II indicates the composition in weight-% of the impregnation solution for each of examples 1 to 13, all these compositions containing between 2 and 15 % by weight of an agent reducing the exudation.

TABLE II

| Components | EXAMPLES | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| DDVP | 70 | 70 | 70 | 70 | 70 | 70 | 70 | 70 | 70 | 70 | 70 | 70 | 70 |
| di-(ethylhexyl) phthalate | 10 | 10 | 10 | 10 | 10 | 10 | 10 | 13 | 12 | 10 | | 10 | 10 |
| epoxidised soybean oil | 14.5 | 14.5 | 14.5 | 14.5 | 14.5 | 14.5 | 14.5 | 14.5 | 14.5 | 14.5 | 14.5 | 14.5 | 14.5 |
| Diazene stabiliser D | 0.5 | 0.5 | 0.5 | 0.5 | 0.5 | 0.5 | 0.5 | 0.5 | 0.5 | 0.5 | 0.5 | 0.5 | 0.5 |
| 2,4-Dimethylphenol | 5 | | | | | | | | | | | | |
| 3,4-Dimethylphenol | | 5 | | | | | | | | | | | |
| 6-ter-butyl-2,4-dimethyl-phenol | | | 5 | | | | | | | | | | |
| Thymol | | | | 5 | | | | | | | | | |
| Carvacrol | | | | | 5 | | | | | | | | |
| 1-Methyl-naphthalene | | | | | | 5 | | | | | | | |
| 2-Naphthylmethyl-ether | | | | | | | 5 | | | | | | |
| 2-Naphthylethyl-ether | | | | | | | | 2 | 3 | 5 | 15 | | |
| 2-Propyl-phenol | | | | | | | | | | | | 5 | |
| 2,3-Dimethylnaphthalene | | | | | | | | | | | | | 5 |

In each series the evaporators were kept in an oven at 40°C in groups of 12 units and at the end of certain periods of time given in Table III, infra, the maximum exudation of the group was determined in the same fashion as in the comparative examples.

The results given in milligrams of DDVP are indicated in Table III.

TABLE III

| Storage time at 40°C | EXAMPLES | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| 1 month | 29 | 38 | 9 | 41 | 6 | 23 | 11 | — | — | — | — | 16 | 14 |
| 2 months | 18 | 91 | 5 | 43 | 6 | 30 | 9 | — | — | 9 | 9 | 38 | 20 |
| 3 months | 40 | — | — | 31 | — | 51 | 11 | 36 | 14 | 16 | 13 | 105 | 11 |
| 4 months | 58 | 122 | 17 | 65 | 21 | 16 | — | 19 | 14 | 16 | 12 | — | — |
| 5 months | — | — | — | — | 15 | — | 18 | 22 | 13 | 9 | — | — | 27 |
| 6 months | 40 | — | — | 74 | — | 17 | 13 | 11 | — | — | — | — | — |

By comparison between the results of Table II and those of the comparative example

| EXAMPLE | 1 | 2 | 3 | 4 | 5 | 6 | 7 | 8 | 9 | 10 | 11 | 12 | 13 |
|---|---|---|---|---|---|---|---|---|---|---|---|---|---|
| Reduction of exudation in % relative to the control evaporators (comparative example) | 91 | 78 | 97 | 89 | 97 | 92 | 97 | 95 | 97 | 97 | 97 | 86 | 96 |

The critical nature of the limits of the value of the expression $$\log P + 7.5 \frac{\mu \cdot d_4^{25}}{\epsilon} \qquad (A)$$

is demonstrated by the comparison with the following substances which were added in an amount of 5 % by weight calculated on the total weight of the liquid impregnation composition.

The vapour pressure of the substances noted below is less than 0.2 Torr at 25°C.

A reduction of exudation when occurring is expressed in percentages calculated on the average exudation of the control evaporators (comparative example).

TABLE IV

| Compound | Value of the expression | Observation |
| --- | --- | --- |
| A. 1-chloromethyl-napthalene | 3.6 | strong exudation |
| B. benzylacetone | 3.6 | strong exudation |
| C. valerophenone | 3.6 | 13% reduction |
| D. di-ethylphthalate | 3.7 | strong exudation |
| E. acetophenone | 3.8 | 25% reduction |
| F. p-anisaldehyde | 3.81 | strong exudation |
| G. methylnonylketone | 3.67 | strong exudation |
| H. ethylbenzoate | 4.7 | 20% reduction |
| I. dodecane | 2.11 | 15% reduction |
| J. diphenyl methane | 1.96 | strong exudation |
| K. diphenylether | 3.9 | strong exudation |
| L. biphenyl | 1.6 | strong exudation |
| M. ethylphenylketone | 3.55 | strong exudation |
| N. methyl salicylate | 4.2 | strong exudation |
| O. diethyl fumarate | 4.7 | strong exudation |
| P. ethyl laurate | 4.1 | strong exudation |
| Q. symmetrical tetrabromethane | 5.4 | strong exudation |

The critical nature of the limit of vapour pressure given under (ii) is demonstrated by comparison with the following substances which were added in an amount of 5 % by weight calculated on the total weight of the liquid impregnation composition.

Although the fact that the value of the expression:

$$\log P + 7.5 \frac{\mu \cdot d_4^{25}}{\epsilon} \qquad (A)$$

in these substances falls within the limits given above under (ii), there was observed visually in each case an exudation, which was about as strong as that of the control evaporators.

TABLE V

| Substance | Value of the expression | Vapour Preessure |
| --- | --- | --- |
| 1. 1,2,4-trichlorobenzene | 3.23 | 0.29 |
| 3. p-isopropyl-toluene | 3.2 | 1.59 |

TABLE V-continued

| Substance | Value of the expression | Vapour Preessure |
| --- | --- | --- |
| 4. cis-decaline | 2.87 | 0.74 |

EXAMPLES 14 TO 22

Nine series of evaporators were manufactured only differing from that of the comparative example by the composition of the impregnation solution. Table VI indicates the composition in % by weight of the impregnation solution for each of Examples 14 to 22, all these compositions containing a combination of two compounds reducing the exudation according to the invention.

TABLE VI

| Components | EXAMPLES | | | | | | | | |
| --- | --- | --- | --- | --- | --- | --- | --- | --- | --- |
| | 14 | 15 | 16 | 17 | 18 | 19 | 20 | 21 | 22 |
| Technical DDVP | 70 | 70 | 70 | 70 | 70 | 70 | 70 | 70 | 70 |
| di-(ethylhexyl) phthalate | 13 | 11 | 8 | 8 | 11 | 11 | 11 | 11 | 11 |
| epoxidised soybean oil | 14.5 | 14.5 | 14.5 | 14.5 | 14.5 | 14.5 | 14.5 | 14.5 | 14.5 |
| metalliferous azoic stabilising dye D | 0.5 | 0.5 | 0.5 | 0.5 | 0.5 | 0.5 | 0.5 | 0.5 | 0.5 |
| 2-naphthylethylether | 1 | 2 | 2 | 5 | 2 | 2 | — | — | — |
| 1-methylnaphthalene | 1 | 2 | 5 | 2 | — | — | 2 | 2 | — |
| 2,4-dimethylphenol | — | — | — | — | 2 | — | 2 | — | 2 |
| thymol | — | — | — | — | — | 2 | — | 2 | 2 |

In each series the evaporators were stored in an oven at 40°C in groups of 12 units and at the end of a certain time the maximum exudation of the group was determined in the same manner as in the comparative example.

The results expressed in milligrams of DDVP are indicated in Table VII.

TABLE VII

| Storage time at 40°C | EXAMPLES | | | | | | | | |
| --- | --- | --- | --- | --- | --- | --- | --- | --- | --- |
| | 14 | 15 | 16 | 17 | 18 | 19 | 20 | 21 | 22 |
| 1 month | — | 11 | — | 11 | 11 | 10 | 10 | 30 | 9 |
| 2 months | 90 | — | 22 | — | 15 | 11 | 15 | 118 | 40 |
| 3 months | 95 | 32 | 11 | 13 | 42 | — | — | — | — |
| 4 months | — | 27 | 11 | 19 | — | 27 | 57 | — | 78 |
| 5 months | — | 33 | — | 16 | — | 27 | 57 | — | 79 |
| 6 months | — | — | 11 | 22 | — | — | — | — | — |

By comparison between the results of Table VII and those of the comparative example one can determine the order of magnitude of the percentage reduction of exudation for those of the compositions tested which correspond to the characteristics of the invention.

| EXAMPLE | 14 | 15 | 16 | 17 | 18 | 19 | 20 | 21 | 22 |
| --- | --- | --- | --- | --- | --- | --- | --- | --- | --- |
| Reduction of exudation in % relative to the control evaporators (comparative example) | 77 | 95 | 97 | 97 | 94 | 96 | 93 | 78 | 89 |

EXAMPLES 23 TO 33

11 series of evaporators were made differing from that of the comparative example only in the composition of the impregnation solution. Table VIII indicates the composition in % by weight of the impregnation solution for each of examples 23 to 33, these compositions only containing a single first additional compound defined under i (b).

| Components | EXAMPLES | | | | | | | | | | |
|---|---|---|---|---|---|---|---|---|---|---|---|
| | 23 | 24 | 25 | 26 | 27 | 28 | 29 | 30 | 31 | 32 | 33 |
| DDVP | 70 | 70 | 70 | 70 | 70 | 70 | 70 | 70 | 75 | 75 | 75 |
| diazene stabiliser D | 0.5 | 0.5 | 0.5 | 0.5 | 0.5 | 0.5 | 0.5 | 0.5 | 0.5 | 0.5 | 0.5 |
| epoxidised cyclohexyl stearate | | | | 29.5 | 19.5 | 19.5 | | | 10 | 10 | |
| epoxidised soybean oil | 29.5 | 19.5 | 19.5 | | | | | | 14.5 | 14.5 | 14.5 |
| glycidyl ether of n-dodecanol | | | | | | | 29.5 | 19.5 | | | |
| isobutylbenzoate | | | | | | | | | 23.5 | 13.5 | 13.5 |
| morpholinothiobenzothiazol | | | | | | | | | 1 | 1 | 1 |
| 6-tert.-butyl-2,4-dimethylphenol | | | | | | 10 | | 10 | | | |
| resorcinol | | | 10 | | | | | | | | 10 |
| carvacrol | | 10 | | | | | | | | | |
| methyl-naphthalene | | | | | | | | | | | |
| 2-naphthylmethylether | | | | | 10 | | | | | | |
| 2-naphthylethylether | | | | | | | | | | 10 | |

In each series the evaporators were stored in an oven at 40°C in groups of 12 units and at the end of a certain time the maximum exudation of the group was determined in the same fashion as in the comparative example.

The results expressed in milligrams of DDVP are indicated in Table IX.

Numerous tests of the efficacy on domestic flies carried out in closed rooms of 30m³ have shown that the devices according to the invention have a regular and prolonged effect similar to that of the evaporators of the comparative example. On the other hand numerous dosages of DDVP in the device, in storage while closed, and in service, in an atmosphere of 65 to 70 % relative

TABLE IX

| Time of storage at 40°C | EXAMPLES | | | | | | | | | | |
|---|---|---|---|---|---|---|---|---|---|---|---|
| | 23 | 24 | 25 | 26 | 27 | 28 | 29 | 30 | 31 | 32 | 33 |
| 1 month | 515 | 6 | 5 | 725 | 7 | 6 | 595 | 6 | 182 | 24 | 19 |
| 2 months | | | | | | | | | 330 | 15 | 26 |
| 3 months | 715 | 9 | 5 | 1100 | 7 | 5 | 332 | 66 | | | |
| 4 months | 772 | 21 | 11 | | 42 | 11 | 785 | 29 | 274 | 62 | 48 |

By comparison between the results of Table VII and those of the comparative examples the order of magnitude of the percentages reduction of exudation is determined for those of the compositions tested which correspond to the characteristics of the invention.

| EXAMPLE: | | | | | | | |
|---|---|---|---|---|---|---|---|
| Reduction of exudation in % relative to | 24 | 25 | 27 | 28 | 30 | 32 | 33 |
| control evaporators | 98 | 99 | 98 | 99 | 94 | 87 | 88 |
| Comparative example (test trial) | 23 | 23 | 26 | 26 | 29 | 31 | 31 |

A similar reduction in exudation is also obtained if DDVP is replaced in the preceding examples by another volatile insecticidal phosphoric ester from the list given above according to formula IV in the same quantity. Although DDVP is used in these examples in quantities of 70 or 75 % by weight, similar results are obtained in the case where DDVP or another insecticidal ester selected from those mentioned above is used in a different quantity between 40 and 90 % by weight. Below 40 % the exudation becomes negligible. When using an elevated quantity of insecticidal ester it is recommended to increase correspondingly the quantity of additional compound defined under (ii) used.

humidity have shown that in the devices according to the invention the stability of the insecticidal active material is just as good as in the evaporators of the comparative example.

The invention permits reduction of inconvenient exudation, which occurs in the course of long time storage in evaporative devices using DDVP and comprising a non-porous polyolefin diffusion layer, to such a degree that it is not detectable by the user, and this without affecting the regularity of functioning of the device and the stability of the insecticidal phosphoric ester in the latter.

We claim:
1. In an insecticidal evaporator comprising
   I an absorbent fibrous mass substrate impregnated with a liquid composition comprising
   a. from about 40 to 90% by weight of the total liquid composition of 2,2-dichlorovinyldimethylphosphate
   b. an epoxidised organic liquid compound having a maximum vapor pressure no greater than the vapor pressure of 2,2-dichlorovinyldimethylphosphate; and
   c. an organic compound which is miscible with or soluble in the mixture of 2,2-dichlorovinyldimethylphosphate and said epoxidised organic com- pound; and

II a non-porous, olefin polymer diffusion layer covering at least part of said impregnated fibrous mass, the remaining surface of said fibrous mass being covered by an envelope impermeable to said liquid composition;

said epoxidised organic compound promoting the exudation of 2,2-dichlorovinyldimethylphosphate at the exterior surface of said diffusion layer, the improvement comprising a method of reducing exudation of 2,2-dichlorovinyldimethylphosphate at the exterior surface position, by incorporating into the liquid composition as the organic compound (c), from about 1 to about 40% by weight of said composition, of an exudation-reducing agent selected from the group consisting of (1) a compound of the formula $$(R)_n \underset{X_2}{\overset{X_1}{\bigcirc}}$$

in which $X_1$ represents hydrogen, $X_2$ represents hydrogen or one of the substituents defined for $(R)_n$, or $X_1$ and $X_2$ jointly represent a divalent bridge of the formula

—CH=CH—CH=CH— and $(R)_n$ represents substitution on the nucleus of members selected from the group consisting of
- ($\alpha$) 2 or 3 hydroxyl groups,
- ($\beta$) from 1 to 3 alkyl groups each having from 1 to 4 carbon atoms,
- ($\gamma$) 1 or 2 alkyl groups each having from 1 to 4 carbon atoms, conjointly with a hydroxyl group, and
- ($\delta$) an alkoxy group having from 1 to 4 carbon atoms, one of which members may occupy the $X_2$ position, and (2) di-(2-chloroethoxy)-methane.

2. The improvement of claim 1 in which the epoxidised organic liquid compound is selected from the group consisting of an epoxidised unsaturated vegetable oil, a glycidyl ether of an aliphatic monoalcohol, a glycidyl ether of a diol and an epoxidised ester of a mono- or dicarboxylic aliphatic acid having from 6 to 24 carbon atoms.

3. The improvement of claim 1 wherein the exudation reducing agent is di-(2-chloroethoxy)-methane.

4. The improvement of claim 1 in which the exudation reducing agent is 2-ethoxynaphthalene.

5. The improvement of claim 1 in which the exudation reducing agent is 2-methoxynaphthalene.

6. The improvement of claim 1 in which the exudation reducing agent is hydroquinone.

7. The improvement of claim 1 in which the exudation reducing agent is resorcinol.

8. The improvement of claim 1 in which the exudation reducing agent is present in an amount ranging from 3 to 10% by weight calculated on the total weight of the composition (I).

* * * * *